US008545400B2

(12) United States Patent
Iijima (10) Patent No.: US 8,545,400 B2
(45) Date of Patent: Oct. 1, 2013

(54) ENDOSCOPE

(75) Inventor: Kazuo Iijima, Musashino (JP)

(73) Assignee: Olympus Medical Systems Corp., Tokyo (JP)

( * ) Notice: Subject to any disclaimer, the term of this patent is extended or adjusted under 35 U.S.C. 154(b) by 942 days.

(21) Appl. No.: 12/255,790

(22) Filed: Oct. 22, 2008

(65) Prior Publication Data

US 2009/0048490 A1    Feb. 19, 2009

Related U.S. Application Data

(63) Continuation of application No. PCT/JP2007/052820, filed on Feb. 16, 2007.

(30) Foreign Application Priority Data

Apr. 24, 2006   (JP) .............................. 2006-119775

(51) Int. Cl.
*A61B 1/06*        (2006.01)

(52) U.S. Cl.
USPC ........... 600/164; 600/165; 600/171; 600/176; 600/177; 600/178

(58) Field of Classification Search
USPC ................. 600/160, 171, 176, 177, 178, 179, 600/181, 164, 109, 129, 170, 175, 182
See application file for complete search history.

(56) References Cited

U.S. PATENT DOCUMENTS

| 4,415,240 | A | * | 11/1983 | Nishioka et al. ................ | 385/33 |
| 4,779,130 | A | * | 10/1988 | Yabe ............... | 348/76 |
| 5,193,525 | A | * | 3/1993 | Silverstein et al. ........... | 600/125 |
| 5,305,736 | A | * | 4/1994 | Ito ............... | 600/109 |
| 6,503,196 | B1 | * | 1/2003 | Kehr et al. ................ | 600/176 |
| 7,108,657 | B2 | * | 9/2006 | Irion et al. ................ | 600/110 |
| 7,267,647 | B2 | * | 9/2007 | Okada et al. ................ | 600/166 |

FOREIGN PATENT DOCUMENTS

| EP | 1 371 321 A1 | 12/2003 |
| JP | 07-031581 | 2/1995 |
| JP | 08-252213 | 10/1996 |
| JP | 2001-166233 | 6/2001 |
| JP | 2001-258823 | 9/2001 |
| JP | 2004-033587 | 2/2004 |
| WO | WO 99/16341 | 4/1999 |
| WO | WO 2006/004124 A1 | 1/2006 |
| WO | WO 2006/011422 A1 | 2/2006 |

OTHER PUBLICATIONS

Communication mailed Mar. 25, 2011 from the European Patent Office in corresponding European Patent Application No. 07714350.1.

* cited by examiner

*Primary Examiner* — Alireza Nia

(74) *Attorney, Agent, or Firm* — Scully, Scott, Murphy & Presser, P.C.

(57) ABSTRACT

An endoscope of the present invention includes an insertion section including a distal end portion, an objective lens placed in the distal end portion, an illumination lens which is placed in the distal end portion adjacently to the objective lens and emits illumination light from a light source, and a wall portion which is placed between the objective lens and the illumination lens, and shields the illumination light, and thereby, secures a sufficient illumination range for an image pickup range with a wide field of view, can obtain a favorable endoscope image and can reduce the diameter.

8 Claims, 5 Drawing Sheets

ENDOSCOPE

CROSS REFERENCE TO RELATED APPLICATION

This application is a continuation application of PCT/JP2007/052820 filed on Feb. 16, 2007 and claims benefit of Japanese Application No. 2006-119775 filed in Japan on Apr. 24, 2006, the entire contents of which are incorporated herein by this reference.

BACKGROUND OF THE INVENTION

1. Field of the Invention

The present invention relates to an endoscope including an illumination section and an image pickup section with a wide view angle.

2. Description of the Related Art

In recent years, endoscopes have been widely used in the medical field and the like. With an endoscope, an organ or the like in a body cavity can be observed by inserting an elongated insertion section into the body cavity, for example, and various kinds of treatment can be made by using a treatment instrument inserted into a treatment instrument insertion channel in accordance with necessity. Further, a bending section is provided at a distal end of an insertion section, and the observation direction of an observation window at a distal end portion can be changed by operating an operation section of the endoscope.

In the endoscope, an optical unit for image pickup including an objective optical system is placed at the distal end portion, and an illumination optical system to be a radiation section of an illumination light source is placed in the vicinity adjacent to the objective optical system. Like this, in the endoscope in which the objective optical system and the illumination optical system are adjacent to each other, illumination light directly enters an objective lens, or intense reflection light from an object enters the objective lens at the time of close observation or the like, and harmful light beams may be photographed, which exerts an adverse effect on an endoscope image, such as halation in which a part of the image becomes white and vague, and lens flare which is the phenomenon in which circular or hexagonal light appears on the a screen by the internal reflection of the lens.

As the countermeasures against such harmful light beams due to illumination, for example, Japanese Patent Application Laid-Open Publication No. 2001-258823 discloses the endoscope in which a plurality of illumination optical systems constituted of wide distribution light and narrow distribution light with the radiation light quantities changed are placed in the periphery of the objective optical system.

Further, some of the conventional endoscopes include wide view angles of, for example, 140° or more at which an endoscope image in a wider range can be photographed than with the conventional view angle of about 120°. In order to realize such a wide view angle, a convex meniscus lens is sometimes used for the objective optical system exposed to the distal end portion of the endoscope. Further, in the illumination optical system, an effective illumination range in which an endoscope image range with a wide angle can be sufficiently illuminated is set.

SUMMARY OF THE INVENTION

An endoscope of the present invention includes an insertion section including a distal end portion, an objective lens placed in the distal end portion, an illumination lens which is placed in the distal end portion adjacently to the objective lens, and emits illumination light from a light source, and a wall portion which is placed between the objective lens and the illumination lens, and shields the illumination light.

DESCRIPTION OF THE PREFERRED EMBODIMENT(S)

Hereinafter, embodiments of the present invention will be described with reference to the drawings.

(First Embodiment)

Figure 1:
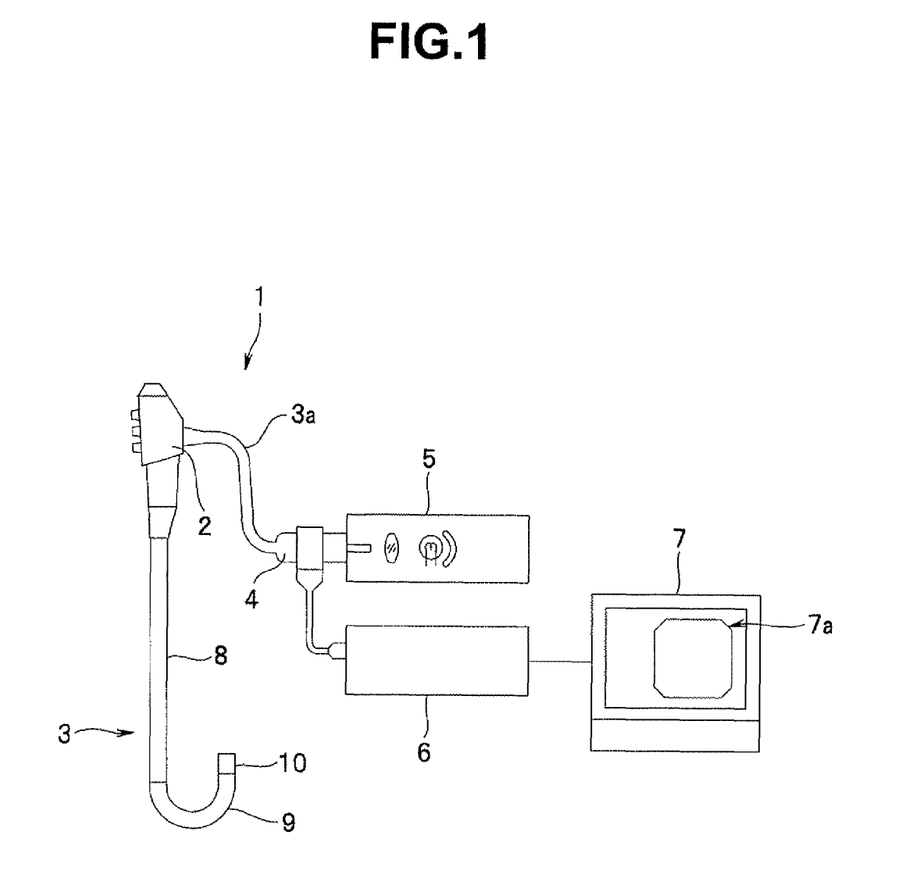
FIG. 1 is a view schematically showing an endoscope apparatus according to a first embodiment of the present invention.
Figure 2:
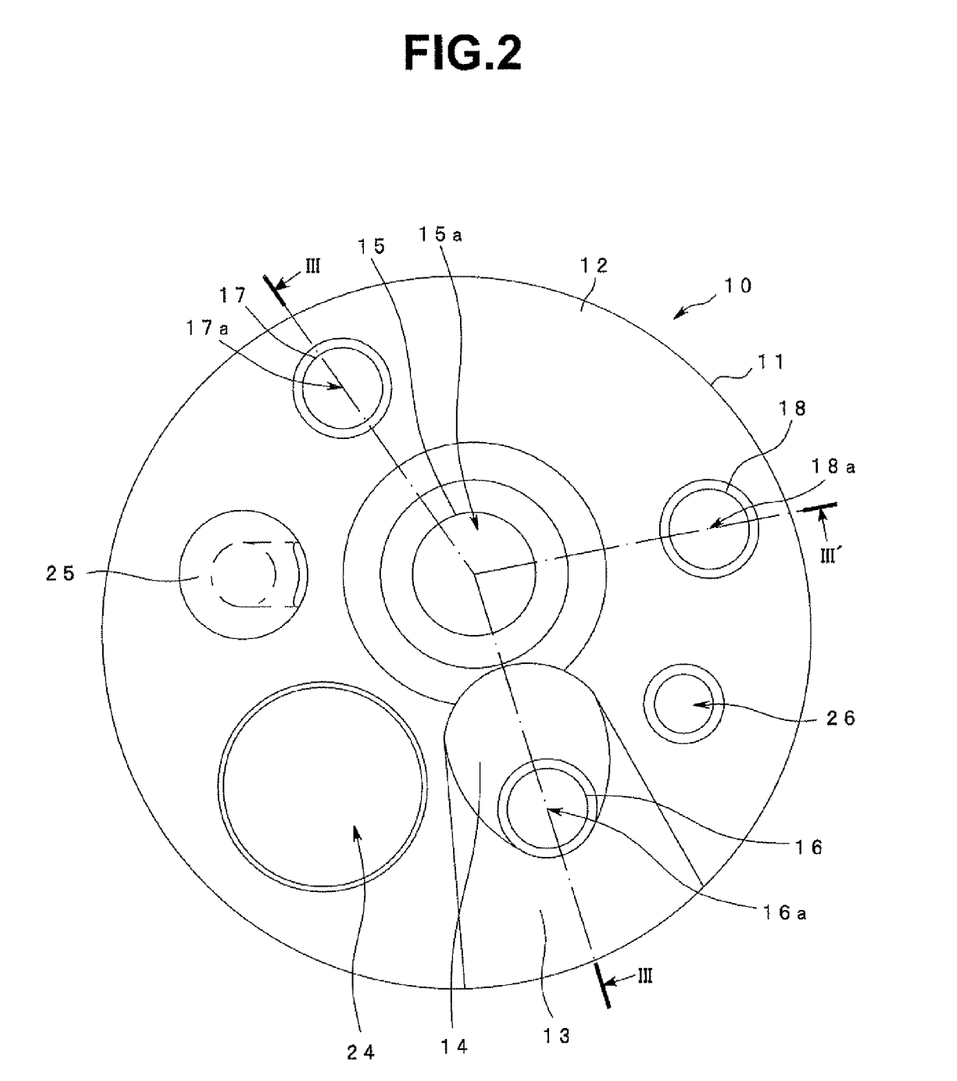
FIG. 2 is a plane view showing a distal end surface of an insertion section of an endoscope of the same.
Figure 3:
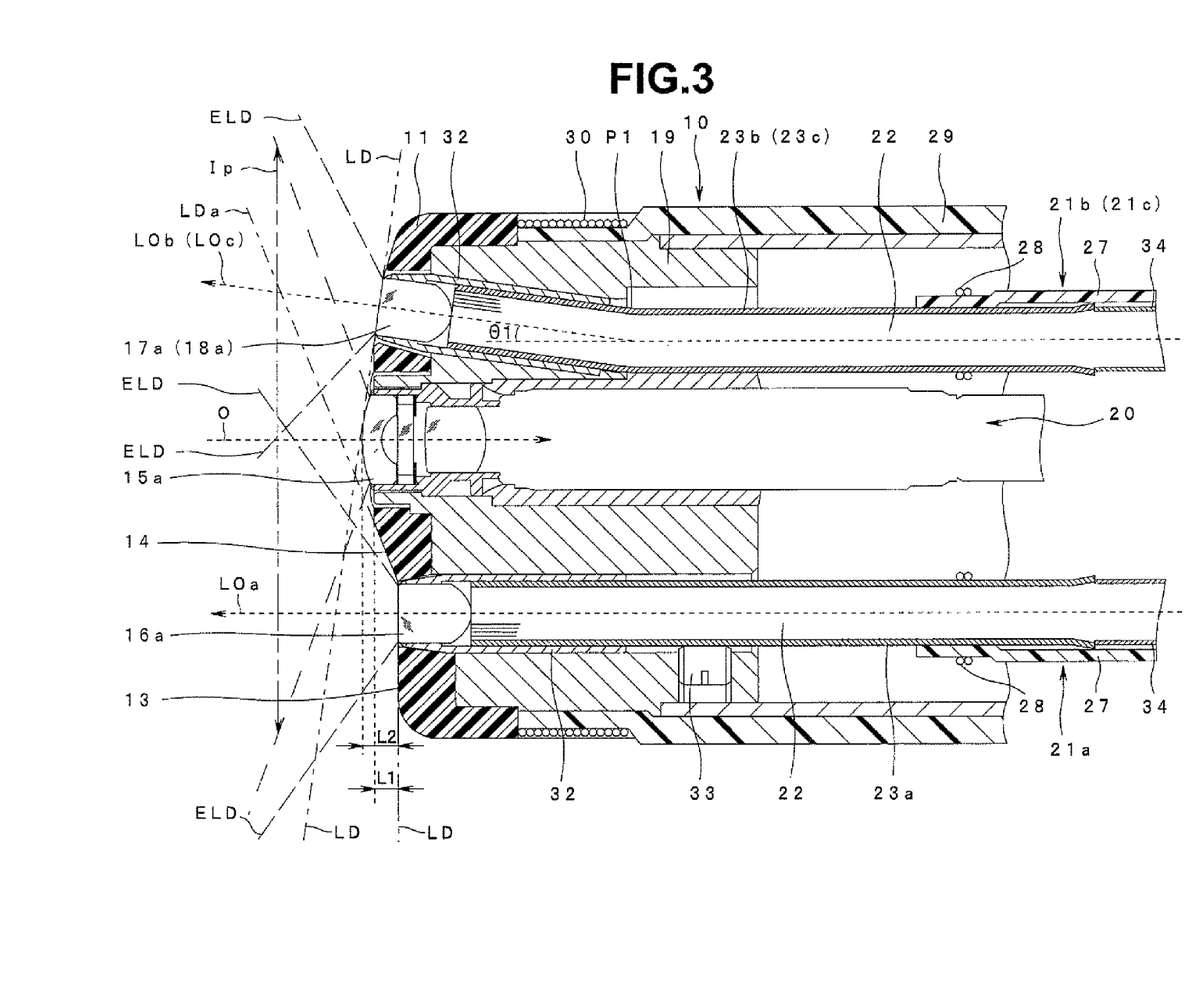
FIG. 3 is a sectional view showing a distal end portion of the insertion section cut along the III-III (III-III') line of FIG. 2, of the same.

FIGS. 1 to 3 relate to an endoscope of a first embodiment of the present invention, FIG. 1 is an explanatory view schematically showing an endoscope apparatus, FIG. 2 is a plane view showing a distal end surface of an insertion section of the endoscope, and FIG. 3 is a sectional view showing a distal end portion of the insertion section cut along the III-III (III-III') line of FIG. 2.

First, based on FIG. 1, a configuration of the endoscope apparatus according to the present embodiment will be described.

As shown in FIG. 1, the endoscope apparatus according to the present embodiment includes an electronic endoscope (hereinafter, simply called as "endoscope") 1, a light source device 5, a processor 6 and a monitor 7. The endoscope 1 includes an operation section 2 which performs a bending operation and control of various conduit lines, an insertion section 3 which is inserted into a body cavity with its proximal end side connected to the operation section 2, and a universal cord 3a which is extended from the operation section 2 and has a connector section 4 at its distal end, and the light source device 5 and the processor 6 are connected to the connector section 4. The monitor 7 is connected to the processor 6.

Further, the insertion section 3 of the endoscope 1 has a flexible tube portion 8 having flexibility, a bending portion 9 provided at a distal end side of the flexible tube portion 8, and a distal end portion 10 provided at a distal end side of the bending portion 9. A distal end surface of the distal end portion 10 is formed into a substantially shell shape, and an image pickup unit 20 (see FIG. 3) is incorporated in an inside.

The image pickup unit 20 has an image pickup device such as a CCD and CMOS, which picks up an image of a region in a body cavity, and an image signal picked up by the image pickup device is transmitted to the processor 6 via the universal cord 3a. In the processor 6, the transmitted image signal is subjected to signal processing, and an image 7a is displayed on the monitor 7.

Further, in the operation section 2, an operation knob for bending the bending portion 9 remotely, a pressure button switches and the like for performing various operations represented by air supply and water supply are placed.

The light source device 5 has an illumination light source, and is connected to a light guide (not illustrated) placed in the operation section 2, the insertion section 3 and the universal cord via the connector section 4. Further, in the present embodiment, an air supply and water supply source and a suction source which perform air supply and water supply, and suction for the conduit lines placed in the endoscope 1 are incorporated in the light source device 5.

As shown in FIG. 2, an objective lens 15*a* placed in an observation window 15, illumination lenses 16*a*, 17*a* and 18*a* which are placed in, for example, three illumination windows 16, 17 and 18 and are illumination means, a suction port 24 which also functions as an opening for a treatment instrument and the like, an air supply and water supply nozzle (hereinafter, simply called a water supply nozzle) 25 for washing contamination of the objective lens 15*a* by performing air supply and water supply when the insertion section 3 is inserted into a body cavity, a forward water supply nozzle 26 for washing blood, mucus and the like of a patient in the body cavity are placed in a distal end surface (distal end surface of a distal end cover 11 which will be described later) 12 of the distal end portion 10. Accordingly, on the distal end surface of the distal end portion 10, a plurality of openings for placing the objective lens 15*a*, the three illumination lenses 16*a*, 17*a* and 18*a*, the suction port 24, the water supply nozzle 25 and the forward water supply nozzle 26 are provided.

The respective illumination lenses 16*a*, 17*a* and 18*a* are disposed in the vicinity of a peripheral edge portion of the objective lens 15*a*. Further, among the respective illumination windows 16, 17 and 18, the suction port 24, the water supply nozzle 25 and the forward water supply nozzle 26 are placed at respective predetermined positions.

More specifically, in the present embodiment, the suction port 24 and the water supply nozzle 25 are placed between the illumination lens 16*a* and the illumination lens 17*a*, and the forward water supply nozzle 26 is placed between the illumination lens 16*a* and the illumination lens 18*a*.

The cap-shaped distal end cover 11 formed from a synthetic resin configuring the distal end surface 12 of the insertion section 3 of the endoscope 1 is placed on the distal end portion 10 of the present embodiment.

In the distal end cover 11, a recessed portion 13 is formed in a periphery of the illumination lens 16*a* placed in the illumination window 16, and a slope portion 14 which is a light shielding wall portion extending from the periphery of the illumination window 16 toward the direction of the objective lens 15*a* is formed.

Next, based on the sectional view of FIG. 3, an internal configuration of the distal end portion 10 will be described.

As shown in FIG. 3, an inside of the distal end portion 10 is provided with a distal end rigid portion 19 in which a space allowing the image pickup unit 20 corresponding to the observation window 15, and the light guides or the like which are illumination components corresponding to the three illumination windows 16, 17 and 18 to be placed inside the distal end portion 10 is formed.

The distal end cover 11 is arranged so as to cover the distal end rigid portion 19, and a distal end side of the distal end rigid portion 19 is covered with the distal end cover 11. The image pickup unit 20 is inserted into the distal end rigid portion 19 and fixed.

The image pickup unit 20 has an observation optical system constituted of the objective lens 15*a*, and a plurality of lenses, a cover glass and an image pickup device such as a CCD and CMOS. The observation view angle by the image pickup unit 20 is set at a wide angle of about 140° or more by a plurality of objective lens groups.

The image pickup device transfers an image signal to the processor 6 by the light incident through the observation window 15, and the processor 6 performs image processing for the received image signal, and generates the data of a substantially rectangular observation image 7*a*. The substantially rectangular observation image 7*a* has four corners of the rectangle cut as shown in FIG. 1, and has a so-called electronic mask applied, and is displayed on the monitor 7 as an octagonal observation image. Here, the optical system of the image pickup unit 20 is designed so that the water supply nozzle 25 does not enter the observation field of view of the image pickup unit 20.

The light guide through which illumination light is guided from the light source device 5 shown in FIG. 1 is inserted through the inside of the insertion section 3 of the endoscope 1. The light guide of the present embodiment is divided into three branches at the distal end portion 10 side, which are respectively inserted through three light guide units 21 (*a*, *b*, *c*) and fixed, in the distal end portion 10.

Among the light guide units 21 (*a*, *b*, *c*), the light guide unit 21*a* is constituted of the illumination lens 16*a* and an optical fiber bundle 22 which is the light guide. A distal end portion of the optical fiber bundle 22 is fixed to an inside of a linear metal pipe 23*a* with an adhesive or the like. In the light guide unit 21*a*, the distal end portion of the optical fiber bundle 22 and the illumination lens 16*a* are inserted in a frame 32 and fixed.

The light guide unit 21*a* is fixed to the distal end rigid portion 19 by a fixing screw 33. The optical fiber bundle 22 from a proximal end side of the metal pipe 23*a* is covered with a flexible tube 34, and further, a part of the metal pipe 23*a* and the tube 34 are covered with an outer tube 27. The outer tube 27 is fixed to the metal pipe 23*a* with a bobbin 28.

Meanwhile, the light guide units 21*b* and 21*c* correspond to the illumination lenses 16*b* and 16*c*, and have the similar configurations to the above described light guide unit 21*a*, and the distal end portion of the optical fiber bundle 22 is fixed to an inside of a metal pipe 23*b* (23*c*) in a bent shape with an adhesive or the like. Though not illustrated, the light guide units 21*b* and 21*c* are also fixed to the distal end rigid portion 19 with the fixing screw 33.

The metal pipe 23*b* (23*c*) is folded to an outer periphery side of the distal end portion 10 at a predetermined angle $\theta 1$ in an intermediate position P1. The angle $\theta 1$ is an angle of for example, about 8°. As a result, the optical fiber bundle 22 is bent along the bent shape of the metal pipe 23*b* (23*c*).

Accordingly, an optical axis LOb (LOc) (hereinafter, the axes will be called illumination optical axes LOb and LOc for convenience of explanation) of the illumination light emitted from the illumination lenses 17*a* and 18*a* irradiating illumination light, the illumination optical axes LOb and LOc are not parallel with an optical axis O (hereinafter, the axis will be called an observation optical axis O for convenience of explanation) incident on the observation optical system such as the objective lens 15*a* and the like of the image pickup unit 20.

Accordingly, the illumination optical axes LOb and LOc are inclined by an angle $\theta 1$ with respect to the observation optical axis O, from the position P1 toward the distal end. Specifically, the distal end directions of the illumination optical axes LOb and LOc are inclined at the predetermined angle $\theta 1$ with respect to the observation optical axis O in the direction away from a point ahead in the observation direction of the observation optical axis O of the image pickup unit. Meanwhile, the illumination optical axis of the light guide unit 21*a* corresponding to the illumination lens 16*a* has an illumination optical axis LOa parallel with the observation optical axis O of the image pickup unit 20.

Further, the proximal end portion of the distal end rigid portion 19 is covered with an outer tube 29 formed by a synthetic resin, rubber or the like. The outer tube 29 is fixed to the distal end rigid portion 19 by a bobbin 30.

The distal end cover 11 is formed into the recessed shape in the periphery of the illumination lens 16a as described above. Specifically, the distal end cover 11 is recessed in a long axis proximal end direction of the distal end portion 10 of the insertion section 3 from the periphery of the illumination lens 16a to an outer peripheral portion by a predetermined length L1 from an edge portion in the vicinity of an outer periphery of the objective lens 15a. Further, the above described slope portion 14 which becomes a surface formed obliquely from the illumination lens 16a to the objective lens 15a is formed in the distal end cover 11.

As for a top portion of the objective lens 15a which is a meniscus lens with a lens surface formed into a convex shape and a lens surface of the illumination lens 16a, the lens surface of the illumination lens 16a is shifted in the proximal end direction by a predetermined distance L2 in the above described long axis direction. In other words, the lens surface of the illumination lens 16a is shifted by the predetermined distance L2 to the incident side of the illumination light from the light source device 5 shown in FIG. 1 with respect to the top portion of the objective lens 15a.

Next, an irradiation operation of the illumination light in photographing of the endoscope image by the endoscope 1 of the present embodiment configured as above will be described.

In the following description, in FIG. 3, an image pickup range Ip in a predetermined focal length where the image pickup unit 20 picks up an image is shown by the two-dot chain line with double end arrows in the drawing. An effective light quantity domain ELD of the illumination light required for photographing of an endoscope image emitted from each of the illumination lenses 16a, 17a and 18a is shown by the broken line in the drawing, and an illumination domain LD (LDa) of the illumination light emitted from each of the illumination lenses 16a, 17a and 18a is shown by the dashed line in the drawing.

The endoscope 1 has the view angle of 140° or more having the image pickup range Ip in the predetermined focal length as described above. The effective light quantity domain ELD of the illumination light emitted from each of the illumination lenses 16a, 17a and 18a is irradiated so that the image pickup range Ip is included.

In this state, irradiation light within the effective light quantity domain ELD emitted in the directions of the illumination optical axes LOb and LOc inclined at the angle $\theta 1$ in the outer peripheral direction of the distal end portion 10 from the two illumination lenses 17a and 18a sufficiently illuminates a periphery of the above described image pickup range Ip.

Meanwhile, the illumination light in the effective light quantity domain ELD emitted in the direction of the illumination optical axis LOa from the illumination lens 16a sufficiently illuminates the above described image pickup range Ip up to and including a central portion of the above described image pickup range Ip. At this time, the illumination light in the effective light quantity domain ELD from the illumination lens 16a illuminates the above described image pickup range Ip including the periphery, and the central portion which cannot be sufficiently illuminated with the effective light quantity domains ELD from the two illumination lenses 17a and 18a.

Thereby, the endoscope 1 of the present embodiment can sufficiently include the central portion of the endoscope image as a result of photographing the image pickup range Ip projected on the observation image 7a of the monitor 7, and the periphery of the image pickup range Ip of the image pickup unit 20 for which a wide view angle (140° or more) is set, in the effective light quantity domain ELD, and therefore, can photograph the object as a bright and favorable image which is easy to see.

Further, the illumination domain LD irradiated by each of the illumination lenses 16a, 17a and 18a illuminates in the direction of substantially 180 degrees with respect to the illumination optical axes LOb and LOc along the respective lens surfaces.

At this time, the two illumination lenses 17a and 18a are inclined at a predetermined angle $\theta 1$ in the direction of the outer periphery of the distal end portion 10, and therefore, the illumination domains LD of the two illumination lenses 17a and 18a are at the forward side from the objective lens 15a. Specifically, the above described predetermined angle $\theta 1$ is the angle at which the illumination light beams emitted to the illumination domains LD of the respective illumination lenses 17a and 18a are not incident on the objective lens 15a.

Meanwhile, the illumination light emitted from the illumination lens 16a is shielded in the emission direction by the slope portion 14 at the side of the objective lens 15a, and is emitted into the illumination domain LDa in the state having a predetermined angle with respect to the lens surface of the illumination lens 16a, along the slope portion 14. Therefore, the illumination light beams of the illumination domain LDa at the side of the objective lens 15a are prevented from being incident on the objective lens 15a.

Thereby, the endoscope 1 of the present embodiment can prevent harmful light beams which exert an adverse effect on the endoscope image, such as halation and lens flare from being photographed as a result of the illumination light directly being incident on the objective lens 15a. Therefore, the endoscope 1 can photograph an object with the endoscope image projected on the observation image 7a of the monitor 7 being a clear and favorable image which is easy to see.

Further, in the endoscope 1, one light guide unit 21a out of a plurality of light guide units 21a to 21c placed in the distal end portion 10 is in a substantially linear shape along the long axis of the distal end portion 10, and therefore, contributes to reduce the outer diameter of the distal end portion 10 without changing the degree of freedom for setting the wide distribution light and narrow distribution light of the illumination light in order to prevent harmful light beams which exert an adverse effect on the endoscope image. The endoscope 1 of the present embodiment can especially prevent incidence of the unnecessary light which exerts an adverse effect on an image on the image pickup unit 20 from the objective lens 15a even when the light quantity of the illumination light is large.

As a result of the above, the endoscope 1 of the present embodiment includes the image pickup unit 20 with a wide angle of 140° or more, and can illuminate the entire range of the image pickup range Ip of the image pickup unit 20 to be bright, and can photograph a clear and favorable image which is easy to see.

(Second Embodiment)

An endoscope 1 of a second embodiment will be described based on FIGS. 4 and 5.

Figure 4:
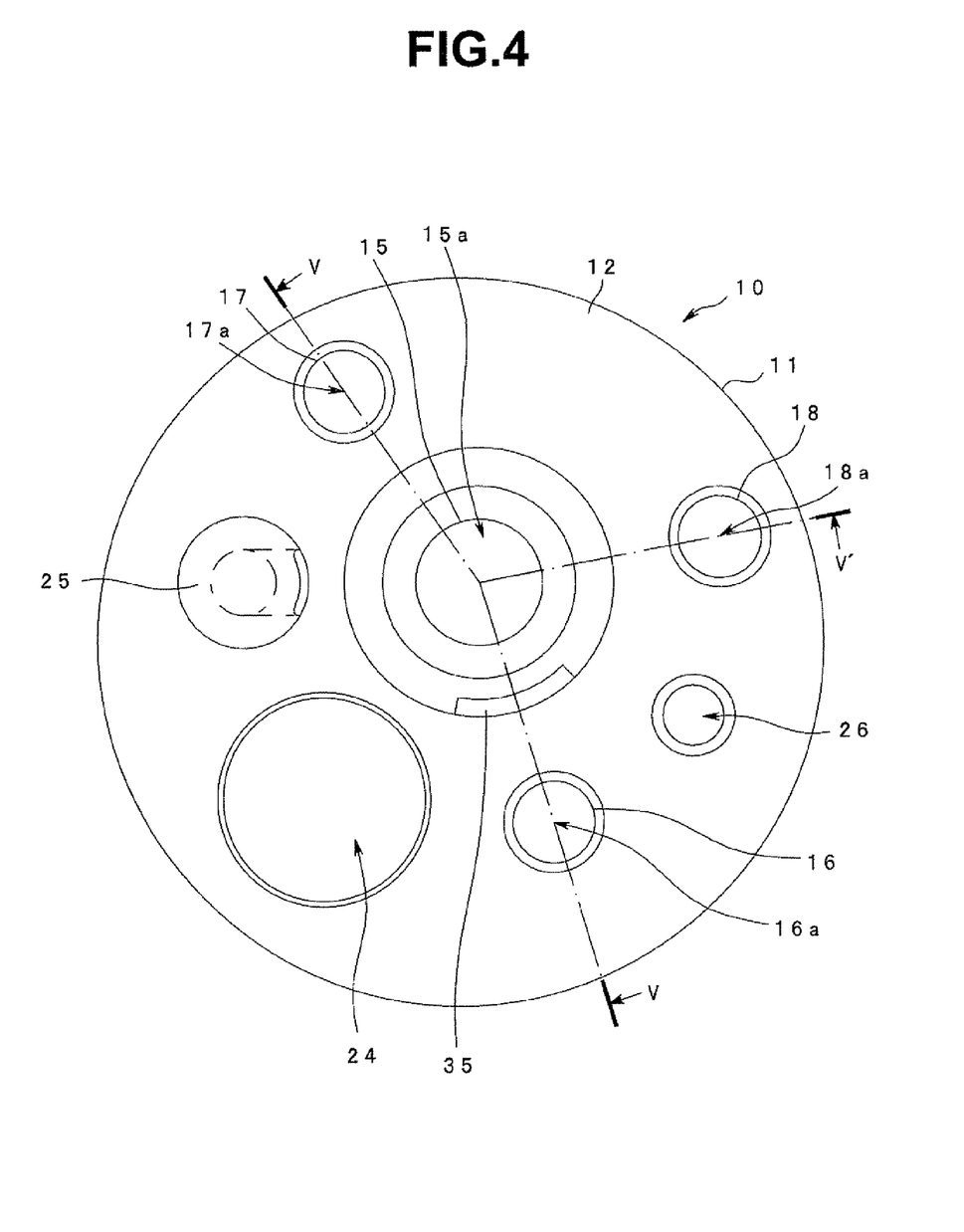
FIG. 4 is a plane view showing a distal end surface of an insertion section of an endoscope according to a second embodiment of the present invention.
Figure 5:
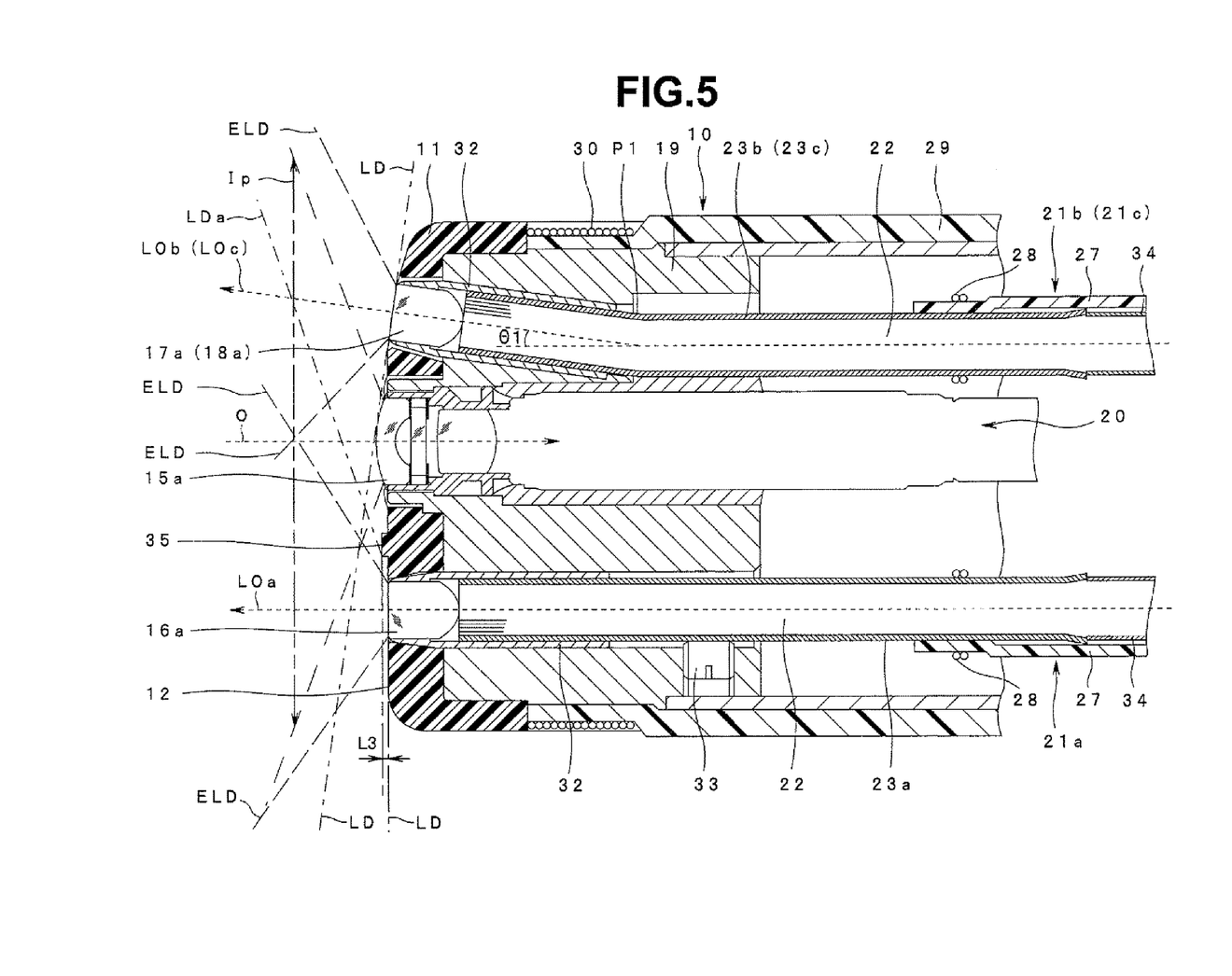
FIG. 5 is a sectional view showing a distal end portion of the insertion section cut along the V-V (V-V') line of FIG. 4, of the same.

FIGS. 4 and 5 relate to the endoscope of the second embodiment, FIG. 4 is a plane view showing a distal end surface of an insertion section of the endoscope, whereas FIG. 5 is a sectional view showing a distal end portion of the insertion section cut along the V-V (V-V') line of FIG. 4. In the following description, the same reference numerals and characters are used for the respective configurations of the endoscope 1 described in the first embodiment, and the explanation thereof will be omitted.

As shown in FIG. 4, the endoscope 1 of the present embodiment has a light shielding wall portion 35 between the objective lens 15a and the illumination lens 16a in the distal end surface 12 of the distal end portion 10.

In the light shielding wall portion 35, its sectional shape along the distal end surface 12, the illumination light from the illumination lens 16a, is in a substantially sector shape having a predetermined circular arc length larger than a diameter of the objective lens 15a. Further, as shown in FIG. 5, the light shielding wall portion 35 is projected from the distal end surface 12 of the distal end portion 10 by a predetermined length L3. Specifically, the light shielding wall portion 35 is a projected portion integrally formed to project in the distal end cover 11.

The endoscope 1 of the present embodiment does not have the recessed portion 13 as described in the first embodiment in the periphery of the illumination lens 16a. Specifically, the lens surface of the illumination lens 16a is disposed in substantially the same plane as the distal end surface 12 of the distal end portion 10.

In the endoscope 1 of the present embodiment configured as above, the illumination light emitted from the illumination lens 16a is shielded in the emission direction at the objective lens 15a side by the light shielding wall portion 35, and is emitted in the illumination domain LDa in the state having a predetermined angle with respect to the lens surface of the illumination lens 16a as in the first embodiment. Therefore, the illumination light beams of the illumination domain LDa at the objective lens 15a side are prevented from being incident on the objective lens 15a.

Further, the above described predetermined length L3 which is the projected amount of the light shielding wall portion 35 from the distal end surface 12 is set so that the illumination light beams of the above described illumination domain LDa are not incident on the objective lens 15a, and is such a length that the illumination light beams of the effective light quantity domain ELD of the illumination lens 16a are not shielded.

As above, the endoscope 1 of the present embodiment provides the similar effect to the first embodiment by placing the light shielding wall portion 35 on the distal end surface 12 between the objective lens 15a and the illumination lens 16a of the substantially linear light guide unit 21a along the long axis of the distal end portion 10.

In each of the above described embodiments, the light quantity of each of the light guide units 21a to 21c may be made the same, or only the light guide unit 21a is configured to guide illumination light with a large quantity of light. Further, the slope portion 14 and the light shielding wall portion 35 which are placed on the distal end surface 12 of the above described distal end portion 10 may be placed between the objective lens 15a, and the other illumination lenses 16b and 16c.

Further, in the configuration of the endoscope 1 of each of the above described embodiments, the diameter of any of the light guide units 21a to 21c may be made larger in order to reinforce the surrounding light quantity of the image pickup range Ip of the image pickup unit 20 with an increase in the angle of the image pickup unit 20.

On the above occasion, harmful light beams which exert an adverse effect on the endoscope image, such as halation and lens flare caused by the close objective lens 15a and the illumination light emitted from any of the illumination lenses 16a to 18a of which diameter is made larger need to be prevented from being incident on the objective lens 15a.

Therefore, in the endoscope 1, the recessed portion 13 and the slope portion 14 may be formed in the periphery of any of the illumination lenses 16a to 18a corresponding to any of the light guide units 21a to 21c of which light quantity is reinforced, of the distal end cover 11, or the light shielding wall portion 35 may be formed between the objective lens 15a and the above described any of the illumination lenses 16a to 18a.

Further, the endoscope 1 of the present embodiment includes the three light guide units 21a to 21c, but the endoscope 1 may have two, or four or more light guide units, or only one light guide unit 21a without being limited thereto.

In place of the light guide units 21 (a, b, c) that are the illumination means, the illumination member by an LED or the like that is a light source may be adopted.

According to the endoscope of the present invention according to each of the embodiments described above, a sufficient illumination range is secured for the image pickup range of the wide field of view, a favorable endoscope image can be obtained, and the diameter can be made small.

Further, the present invention is not limited only to the embodiments described above, but various modifications can be made in the range without departing from the spirit of the present invention.

What is claimed is:

1. An endoscope, comprising:
an insertion section including a distal end provided with a distal end portion;
an objective lens placed in the distal end portion; and
an illumination lens which is provided to each of a plurality of illumination windows placed on a distal end surface of the distal end portion adjacently to the objective lens, and emits illumination light guided by a light source from a proximal end direction of the insertion section;
wherein a first illumination lens is provided to a first illumination window as at least one of the plurality of illumination windows is configured to emit light that includes an optical axis substantially parallel with a photographing optical axis incident on the objective lens,
a second illumination lens is provided to a plurality of second illumination windows different from the first illumination window of the plurality of illumination windows is configured to emit light that includes an optical axis angled with respect to the photographing optical axis in a direction away from the photographing optical axis, and
a sloped wall portion, which shields illumination light from the first illumination lens and shields the illumination light from being incident on the objective lens, is positioned only between the objective lens and the first illumination window.

2. The endoscope according to claim 1, wherein the wall portion is a slope portion formed between the objective lens and the first illumination window, and the wall portion shields illumination light from the first illumination lens when the objective lens is arranged further distally on the distal end portion than the first illumination lens.

3. The endoscope according to claim 1, wherein the wall portion is a projected portion formed between the objective lens and the first illumination window and the wall portion shields illumination light from the first illumination lens when the objective lens is arranged further distally on the distal end portion than the first illumination lens.

4. The endoscope according to claim 1, wherein a quantity of the illumination light from the first illumination lens is larger than a quantity of the illumination light from the second illumination lens.

5. The endoscope according to claim 1, wherein the objective lens has the objective lens surface in a convex shape.

6. The endoscope according to claim 2, wherein the objective lens has the objective lens surface in a convex shape.

7. The endoscope according to claim 3, wherein the objective lens has the objective lens surface in a convex shape.

8. The endoscope according to claim 4, wherein the objective lens has the objective lens surface in a convex shape.

\* \* \* \* \*